United States Patent [19]

Hurley et al.

[11] Patent Number: 4,940,834
[45] Date of Patent: Jul. 10, 1990

[54] PLANTS HAVING ENDOPHYTIO-FUNGUS-ENHANCED PERFORMANCE AND METHOD OF PRODUCING SAME

[75] Inventors: Richard H. Hurley, Flemington; Cyril R. Funk, Jr., East Brunswick, both of N.J.

[73] Assignee: Lofts, Inc., Bound Brook, N.J.

[21] Appl. No.: 558,338

[22] Filed: Dec. 5, 1983

[51] Int. Cl.$^5$ .............................................. A01H 5/00
[52] U.S. Cl. .............................. 800/200; 800/DIG. 8; 800/DIG. 55; 800/250
[58] Field of Search ................................ 47/58; 800/1

[56] References Cited

PUBLICATIONS

Funk, C. R. et al., 1983, An Endophytic Fungus and Resistance to Sod Webworms: Association in Lolium Perenne L. Bio/Tech. 1(2):189.
Funk, C. R. et al., 1983, Implications of Endophytic Fungi in Breeding for Insect Resistance, Proc. Forage and Turfgrass Workshop, pp. 67-75.
C. W. Bacon, et al., 1983, Biology of the Endophyte of Fescue: Ultrastructural Anaylsis and Physiological Relationships, Proc. Forage and Turfgass Workshop, pp. 19-28.
Siegel, M. R. 1983, Detection of the Tall Fescue Endophyte, Proc. Forage and turfgrass Workshop, pp. 63-66.
Lancashire, J. (Chairman), 1983, Ryegrass Staggers, Annual Proc. New Zealand Grassland Assoc., 44:1.
Proceedings Forage & Turfgrass Endophyte Workshop, May 3-4, 1983.
Prestidge, R. A. et al., 1982, An Assocation of Lolium Endophyte with Ryegrass Resistance to Argentine Stem Weevil. Proc. 35th N.Z. Weed and Pest Control Conf., pp. 119-122.
Admad, S. and C. R. Funk, 1983, Bluegrass Billbug (Coleoptera:Curculionidae) Tolerance of Ryegrass Cultivars and Selections, J. Econ. Entomol 73(3):414.
Clay K., 1983, Modes of Infection of the Fungus *Atkinsonella Hypoxylon* (Clavicipitaceae), Submitted to Canadian Journal of Botany.
Sampson, "The Presence of Absence of an Endophytic Fungus in Lolium Temulentum and L. Perenne", pp. 337-343, (1935).
Funk, "An Endophytic Fungus and Resistance to Sod Webworms: Association in Lolium Perenne L.", Bio/-Technology, Apr. 1983, Nature Publishing Co.
Neill, "The Endophyte of Rye-Grass (Lolium Perenne)", The N.Z. Journal of Science and Technology, pp. 280A-291A, (1940).
Lloyd, "The Endophytic Fungus of Perennial Ryegrass," The N.Z. Journal of Science & Technology, (1959), pp. 1187-1194.
Latch, "Ryegrass Endophyte, Incidence and Control", The N.Z. Journal of Science & Technology, (1982), vol. 25, pp. 443-448.
Jones, "The Association of an Endophytic Fungus Sphacelia Typhina (pers) Sacc. with the Production of Pyrrolizidine Alkaloids in Tall Fescue", Thesis, University of Kentrucky, 1981.
Sampson, "The Systemic Infection of Grasses by Epichloe Typhina", 18 Tul. Trans. Brit. Nycol. Soc. 30, (1933).
Sampson, "Further Observations on the Systemic Infection of Lolium", 21 Trans. Brit. Mycol Soc., (1937), pp. 84-97.
Bacon, "Epichloe Typhina from Toxic Tall Fescue Grasses", 34 Appl. Environ. Microbiol., (1977), pp. 576-581.
Report on Proceedings of the Forage & Turfgrass Endophyte Workshop, 1983 in Corvallis, Oregon, Drs. Funk and Hurley.
Johnson, "Detection of Epichloe Typhinan in Tall Fescue by Means of Enzyme-Linked Immunisorbent Assay", 72 Phytopathology 647, (1982).
Mazur, "Reactions of Perennial Ryegrass Varieties to Sod Webworm Larvae", 12 Rutgers Turfgrass Proceedings, 85, (1981).
Prestidge, "An Association of Lolium Endophyte with Ryegrass Resistance to Argentine Stem Weevil", Proc. 35th N.Z. Weed & Pest Control Conference, pp. 199-222, (1982).
Mortimer, "Recent Advances in Ryegrass Staggers", 34 Proceedings Ruakura Farmers Conference 71, (1982).

*Primary Examiner*—Robert E. Bagwill
*Attorney, Agent, or Firm*—William H. Elliott, Jr.

[57] ABSTRACT

A method for developing new varieties of plants which host an endophytic fungus, said fungus conferring enhanced performance on its plant host. The method comprises selecting a maternal parent which hosts an endophytic fungus capable of enhancing its host plant's performance. A paternal parent plant of the same or of a different variety as the maternal parent plant is selected. The selected maternal parent plant is then crossed with the selected paternal parent plant. The progeny of the cross which have the desired enhanced-performance characteristics are themselves selected. These progeny are then sexually or asexually propagated and the seed, vegetative propagules, or disseminules harvested.

2 Claims, No Drawings

PLANTS HAVING ENDOPHYTIO-FUNGUS-ENHANCED PERFORMANCE AND METHOD OF PRODUCING SAME

BACKGROUND OF THE INVENTION

This invention relates to new varieties of plants and the production thereof, and, more particularly, to new varieties of plants having enhanced performance and a method of producing same.

Plant breeders are continually developing new plant varieties in which desirable characteristics and plant performance are optimized. Plant performance is a reflection of the sum total of many factors, including yield or productivity, ecological fitness, appearance, vigor, resistance to weed invasion, recovery from injury, persistence, and density, and can be enhanced by improving pest resistance and tolerance of herbicides, defoliation, heat, and drought.

Resistance to insect predation is an important factor in any given plant's performance. Consequently, plant breeders constantly seek to upgrade the insect resistance of important plant varieties. However, as soon as a new variety of insect-resistant plant is developed, usually after years of painstaking breeding programs, insects may sooner or later evolve that are able to feed, without adverse effect, on the once insect-resistant plant. Thus, the ultimate grower of the new plant variety is faced with a number of alternatives. He can either await further development of a new variety of pest-resistant plant, or turn either to chemical pesticides or biological pest control.

Generally, chemical pesticides are unduly expensive, and quite frequently they have an objectionable environmental impact.

An alternative to the use of chemical pesticides is biological pest control. Perhaps the best known use of biological pest control is the well-publicized case of the screwworm fly. There, the discovery that screwworm flies mated only once led to the method whereby large numbers of laboratory-bred male flies were sterilized by X-ray irradiation. By subsequently releasing these sterile males, the females with which they mated could lay only infertile eggs. Thus, by exploiting the known mating habits of a particular insect pest, its numbers were effectively curtailed. Another example of biological pest control includes the use of insect pathogens, such as certain lethal or debilitating insect viruses. Because these viruses are generally host-specific, the targeted insect pest can be readily controlled without harming beneficial species.

The advantages of biological control of insect pests are several. First, biological controls are generally self-limiting; once numbers of the target species are reduced, so too are the biological controls. Second, biological pest controls are usually host-specific and do not attack desirable species. Finally, and perhaps most importantly, biological pest controls are normally environmentally compatible, unlike chemical pesticides which may persist in the environment and kill indiscriminately.

A new biological pest control has recently been recognized. Certain plants host symbiotic endophytic fungi which confer, among other things, an enhanced resistance to insect predation on the host plant. For example, in perennial rye-grasses, a positive association has been demonstrated between the presence of an endophytic fungus (literally, a fungus living within its plant host) and resistance of the plant to attack by some of the most prevalent insect infestations encountered in the field—i.e. the sod webworm, the bluegrass billbug, the Argentine stem weevil, the Southern armyworm, and the chinch bug.

In particular, perennial ryegrasses of the genus Lolium hosting an endophytic fungus are highly resistant to feeding of the larval stages of the Lepidopteran sod webworms of the genus Crambus. Commonly found Crambus species include *C. mutabilis, C. teterrellus, C. trisectus,* and *C. vulgivagellus*. Plants lacking the endophytic fungus can sustain substantial injury from feeding Crambus larvae. (C. R. Funk et al., 1983, "Implications of Endophytic Fungi in Breeding for Insect Resistance," *Proc. Forage and Turfgrass Endophyte Workshop,* pp. 67-75, and C. R. Funk et al., 1983, "An Endophytic Fungus and Resistance to Sod Webworms: Association in *Lolium perenne* L.," *Bio/Technology* 1(2):189, each incorporated herein by reference.) Resistance in ryegrasses hosting this fungus to feeding of the larval stages of the Coleopteran bluegrass billbug (Sphenophorus spp.) has also been observed. (Funk et al., 1983, *Proc. Forage and Turfgrass Endophyte Workshop,* pp. 67-68.) Finally, in ryegrasses hosting an endophytic fungus we have observed resistance to feeding by the Hemipteran chinch bug (Blissus spp.), and others have observed resistance in ryegrasses hosting endophytic fungus to the Coleopteran Argentine stem weevil (Listronotus spp.). This endophyte-enhanced insect resistance in ryegrasses to three different orders of very prevalent chewing insects (Lepidoptera, Coleoptera, and Hemiptera) provided us with a broad-based mechanism for developing new plants having enhanced performance including resistance to these insects.

The exact mechanism of this enhanced resistance to insect predation has not as yet been identified, although it is suspected that such resistance could involve the generation of chemicals toxic to insects which may be present in plants containing the endophytic fungi. These chemicals might be produced by the endophytic fungus or by the host plants themselves in response to the invading fungus. The latter mechanism may mediate a generalized resistance to insects feeding on plant parts having the highest concentrations of endophytic fungi or their associated toxins.

By way of example, the association of sod webworm resistance with the presence of an endophytic fungus in several varieties, selections, and single-plant progenies of perennial ryegrasses was tested in ryegrass turf trials at Adelphia, N.J. in 1980. Resistance was expressed both as a lack of larval feeding and as a nearly complete absence of larvae from the soil beneath resistant ryegrasses. Results of that test are summarized in Table 1, from C. R. Funk et al., 1983, *Bio/Technology* 1(2):189 at 190. Perennial ryegrass entries containing a high percentage of the endophytic fungus showed resistance to predation by the sod webworm. Ryegrasses susceptible to sod webworm predation contained zero or low levels of the endophyte.

Maternal transmission (seed produced from a mother plant high in endophyte) of insect resistance was dramatically evident in the Adelphia test. All open-pollinated, single-plant progenies descending from lines without endophyte produced susceptible progenies. Progenies produced from seed of each of the single plants could be categorized as either resistant or susceptible; no seedlings were rated as having intermediate susceptibility. Essentially all plants produced by seed harvested from a given single plant were either resistant or susceptible depending on the presence or absence of the endophyte in the mother plant, an unexpected result because perennial ryegrass is a highly heterozygous, cross-pollinated species.

TABLE 1

Association of sod webworm resistance with presence of an endophytic fungus in cultivars, selections, and single-plant progenies of perennial ryegrass.

| | | | Endophyte level in seed | |
|---|---|---|---|---|
| Entry | Percent[a] green turfgrass | Microscopic examination %[b] | ELISA ANALYSIS Endophyte Presence[c] | %[d] |
| Ryegrasses rated as resistant to sod webworms[e] | | | | |
| 1. 79-132 | 95 | 93 | + | 87 |
| 2. 79-140 | 90 | 96 | + | 100 |
| 3. 79-153 | 98 | 97 | + | 90 |
| 4. 79-376 | 98 | 97 | + | 90 |
| 5. Pennant | 87 | 90 | + | 87 |
| 6. SWRC-1 | | 88 | + | 87 |
| 7. 79-130 | 98 | 100 | | |
| 8. 79-141 | 96 | 97 | | |
| 9. 79-157 | 90 | 100 | | |
| 10. 79-249 | 95 | 100 | | |
| 11. 79-361 | 95 | 100 | | |
| 12. GT-II | 96 | 98 | | |
| Ryegrasses rated as susceptible to sod webworms[e] | | | | |
| 13. 79-135 | 15 | 0 | — | |
| 14. 79-137 | 15 | 0 | — | |
| 15. 79-164 | 10 | 0 | ± | 0 |
| 16. 79-244 | 30 | 0 | — | |
| 17. 79-268 | 20 | 0 | ± | 0 |
| 18. 79-136 | 30 | 0 | | |
| 19. 79-146 | 12 | 0 | | |
| 20. 79-159 | 13 | 0 | | |
| 21. 79-269 | 20 | 0 | | |
| 22. 79-389 | 30 | 0 | | |
| 23. Gator | 14 | 2 | | |
| 24. Yorktown II | 16 | 0 | ± | 0 |
| 25. Diplomat | 20 | 0 | — | |

[a]% green turfgrass is an indication of absence of injury by sod webworm larvae.
[b]% infection based on an analysis of 30-50 individual seeds per entry.
[c]ELISA analysis based on 5 lots of 10 seeds each (50 seeds total per entry).
Minus (—): all 5 seed lots negative.
Plus-minus (±): very weak ELISA reactions in 1 or 2 of the 5 seed lots.
Plus (+): all 5 seed lots strongly positive.
[d]% infection based on an analysis of 30 individual seeds per entry.
[e]Resistant ryegrasses had an average of 0.74 sod webworm larvae per 0.1 m², whereas susceptible ryegrasses had from 8.0 to 13.7 sod webworm larvae per 0.1 m².

The observation of maternal transmission of sod webworm resistance is illustrative of enhanced performance due to endophyte-enhanced pest resistance.

In addition to the observed resistance to predation by insects, plants hosting the endophytic fungus have displayed a certain enhanced performance which includes increased yield or productivity, improved ecological fitness, a more attractive appearance, increased vigor, reduced weed invasion, more rapid recovery from injury, improved persistence, increased density, and apparently greater stress tolerance. For example, in turf trials of tall fescue and perennial ryegrass varieties and single-plant progenies established during the late summer of 1976 at North Brunswick, N.J., those varieties containing a high level of endophyte fungus showed dramatically improved performance after seven years. Species tested included tall fescue (*Festuca arundinacea*) and ryegrass (*Lolium perenne*). These plants were more persistent, showed reduced crabgrass invasion, produced a higher yield, had greater vigor, and displayed an improved appearance. Much of this improved performance of these fungal-endophyte-hosting plants appears to be associated with improved stress tolerance, such as tolerance of herbicides, heat, drought, and defoliation. Similar enhanced performance, including resistance to the billbug and the chinch bug, has been observed for hard fescue (*Festuca longifolia*) and for chewings fescue (*Festuca rubra*).

The particular endophytic fungus involved in the above-described insect resistance and enhanced performance in ryegrass has been provisionally designated the Lolium endophyte. A similar or identical endophytic fungus present within tall fescue (*Festuca arundinacea* Schreb.) has been identified as *Epichloe typhina* (Fr.) Tul. and was recently renamed *Acremonium coenophialum* Morgan-Jones and Gams.

The life cycles of endophytic fungi have been studied in detail. (C. W. Bacon et al., 1983, "Biology of the Endophyte of Fescue: Ultrastructural Analysis and Physiological Relationships," *Proc. of the Forage and Turfgrass Endophyte Workshop*, pp. 19–28.) The fungus begins within the seed of the host plant, adjacent to the aleurone layer. When the seed germinates, the fungus spreads into the endosperm, from which the developing embryo derives nutrient, and subsequently into the embryo or developing seedling. Apparently, as the seedling develops strengthening tissue and air spaces, the fungus is able to grow between the plant's cells, i.e. interstitially. In the mature plant, the fungus grows into the rhizomes, leaf seed tissue, flower stem, and seeds, but avoids penetration into the roots.

As a prelude to the invasion of the fungus into its host's developing seed, the fungus concentrates its mycelia in the flower stem. As the seed develops, the fungus grows into the seed adjacent to the aleurone layer, initially avoiding the embryo. Upon germination, invasion of the embryo begins, and the fungus life cycle continues as just described.

SUMMARY OF THE INVENTION

The present invention teaches a method for developing new varieties of plants which host an endophytic fungus, said fungus conferring enhanced performance on its plant host. The method comprises selecting a maternal (seed) parent which hosts an endophytic fungus capable of enhancing its host plant's performance. A paternal (pollen) parent plant, of the same or of a different variety as the seed parent plant, having some desirable characteristic, is selected. The pollen parent may be free of the fungal endophyte, as the endophytic fungus is maternally transmitted. The selected seed parent plant is then crossed with the selected pollen parent plant, and the progeny from that cross which have the desired enhanced-performance characteristics are themselves selected. These progeny are then propagated through any of a number of the following routes.

Selected progeny may be reproduced through sexual and asexual means. Sexual reproduction includes self-pollination and cross-pollination. Asexual reproduction includes vegetative propagation and apomictic reproduction. Once the desired characteristics are incorporated into the new variety, the new variety may be propagated by seed, vegetative propagule, or disseminule.

DETAILED DESCRIPTION OF THE INVENTION

In the preferred embodiment of the invention, a seed parent which hosts a symbiotic plant-performance-enhancing endophytic Ascomycete fungus or Fungi Imperfecti is selected. Fungi of choice are selected from the family Clavicipitaceae or Moniliaceae, and, more particularly, the genera Epichloe and Acremonium, respectively. In a preferred embodiment of the invention, the Lolium endophyte fungus of choice is *Epichloe typhina=Acremonium coenophialum*. Similar activity has been shown in the grass Danthonia hosting an endophyte of the genus Atkinsonella=Balansia. There are indications that the closely related endophytic fungi of the genus Balansiopsis confer similar enhanced performance in their plant hosts. (Classifications based on *The Fungi: An Advanced Treatise*, Vol. IV-A, 1973, Ainsworth, et al., Academic Press.)

The fungus may be detected in its host plant using microscopic examination, enzyme-linked immunosorbent assay (ELISA), isolation in agar, and chemical analysis for fungusinduced alkaloids, the former two methods being preferred for routine analysis. (M. R. Siegel, 1983, "Detection of the Tall Fescue Endophyte," *Proc. of the Forage and Turfgrass Endophyte Workshop*, pp. 63-66, incorporated herein by reference.)

Microscopic examination to establish the presence of the fungus in a selected parent is greatly aided by first differentially staining the fungus in plant structures suspected of harboring the fungus, such as seeds, thereby increasing the contrast between plant structure and fungus. An example of such differential staining is given by Funk et al. in *Bio/Technology* 1(2): 189-190 (1983), whereby seeds are soaked for 15 hours in a 5% NaOH—0.1% trypan blue solution and subsequently cleared and stained by gently boiling the soaked seeds for 12 minutes in lactophenol—0.1% trypan blue. Lactophenol is made up of 1 part lactic acid, 1 part glycerol, 1 part liquified phenol, and 5 parts water. Seeds are then crushed on a microscope slide and examined for the presence of fungal mycelium.

ELISA techniques are described in detail in Johnson et al., 1982, "Detection of *Epichloe typhina* in Tall Fescue by Means of Enzyme-linked Immunosorbent Assay," *Phytopathology* 72:647, incorporated herein by reference.

Once a seed parent plant hosting the endophytic fungus is selected, a pollen parent having a desired genotype is selected. Presence or even absence of endophytic fungus in the pollen parent is not a factor, as the fungus is transmitted directly to the progeny by infecting the seed as it develops on the maternal plant. The selected seed parent and pollen parent are crossed, and the progeny therefrom which have both the desired genotype and the performance-enhancing fungus are selected.

Once progeny from this cross have been selected, sexual and/or asexual breeding techniques best suited to the species of plant involved may be used to further propagate and develop it as a new variety with high levels of endophytic fungus and the desired genotype. The new variety may then be harvested as seed, vegetative propagule, or disseminule and later propagated. Where seeds or disseminules are harvested and then stored for later use, care must be taken to store them under cold, dry conditions. Long-term storage (18 months or more) of fungal-endophyte-infected seed stored under normal storage practices is known to give rise to plants free of endophyte; this is due to lost viability of the fungal endophyte.

There are various well-known vegetative reproduction techniques, such as shoot-tip culture, somatic embryogenesis, and cuttings, which generate large numbers of genetically identical clones of the selected plant. These techniques are ideally suited for instances in which at least one of the progeny from the parental cross exhibits all of the desired characteristics of the parents.

Some plant species reproduce by apomixis, wherein asexual reproduction may be effected by specialized seed-like structures (disseminules) not dependent upon fertilization. Thus, by harvesting the disseminules, offspring which are identical to the parent may be propagated. This method of propagation is best suited for those plants which reproduce by means of facultative apomixis, that is, which may reproduce either sexually or by apomixis. Thus, following the initial cross between parents of a facultatively apomictic variety in which the endophytic fungus is passed to the progeny, the selected progeny may themselves be propagated asexually by apomixis, thereby preserving that progeny's genetic makeup.

Sexual reproduction of selected progeny of the original cross includes self-pollination and cross-pollination. Self-pollination is particularly effective where highly homozygous plants are involved and the propagation of such plants to produce pureline or multiline varieties is desired. It is also possible, in some normally self-pollinated species, to use pureline parents to produce hybrid varieties. Thus, homozygous lines in which the performance-enhancing endophytic fungus has been introduced may be bred true and increased directly by seed for commercial use.

Progeny of the original parental cross may be further developed into still-better varieties by backcrossing and other hybridization programs, provided that a plant containing the desired endophyte is used as the female parent in all crosses. For example, particular characteristics may be further enhanced by crossing a maternal fungal-endophyte-containing plant with the recurrent parent having desirable characteristics. Backcrossing is successively repeated, and desirable progeny from each cross are selected for the desired characteristics. This technique is particularly effective when adding new characteristics to existing desirable plant varieties.

Development of novel enhanced-performance varieties in cross-pollinating species which host the fungus includes the selection and development of a desirable population of interbreeding plants or the development of hybrid varieties. Varieties developed as interbreeding populations are both highly heterogenous and highly heterozygous. They include varieties developed by ecotype selection, mass selection and the production of synthetic varieties. Naturally occurring ecotypes and old land varieties developed and maintained by natural selection and mass selection may include a certain frequency of plants hosting the desired fungus. If such varieties have undergone many generations of random recombination in isolation, the mass selection of a large number of plants hosting the fungus can be used to reconstitute a given variety in one generation. This reconstituted variety will have the gene frequencies and the genetic heterogeneity and heterozygosity of the original variety with the additional advantage of the performance-enhancing fungus. The variety can be further improved by modified backcrossing, recurrent selection, mutation breeding, and genetic engineering.

Mass selection of endophyte-hosting plants can be used to improve synthetic varieties which have otherwise lost their performance-enhancing fungus. As previously described, loss of the fungus can occur following improper or prolonged storage of breeder or foundation seed. Cycles of random recombination in isolation may be needed to insure that this new population of endophyte-containing plants possesses the same gene frequencies, heterogeneity and heterozygosity as the original variety. This should be done prior to the selection of the many endophyte-containing plants needed.

Hybrid varieties hosting the fungal endophyte must be produced from seed parents which host the fungus. Parents of synthetic varieties can be vegetatively propagated from plants selected from fungus-containing populations discovered in nature, cultivated situations, or breeding nurseries produced by hybridization programs, mutation breeding, or genetic engineering programs using female parents containing the desired endophyte.

Particularly suited for the method of the present invention are those plants of the family Graminae (grasses), more particularly those of the genera Lolium, Festuca, Agrostis, and Poa.

EXAMPLE (PERENNIAL RYEGRASS)

In this example, the turf grass variety *Lolium perenne* cv. Repell (experimentally designated as GT-II in Table 1) was developed as an advanced-generation synthetic cultivar selected from the progenies of 27 clones, each of which hosted the performance-enhancing endophytic fungus. Repell can be distinguished from all other varieties of perennial ryegrass by the following unique combination of characteristics: It is a leafy, turf-type perennial ryegrass capable of producing a persistent, dense, attractive, low-growing turf of a bright dark-green color. It has medium seed maturity, medium-fine leaves, excellent wear tolerance, very good heat and drought tolerance, and good cold hardiness. This variety has shown good resistance to the large brown patch disease incited by *Rhizoctonia solani* Kuhn, the winter leaf spot disease caused by Drechslera spp., and many races of crown rust caused by *Puccinia coronata* Corda var. lolii Brown. It hosts a performance-enhancing fungus of the genus Epichloe =Acremonium, and has good resistance to sod webworms, billbugs, and the Argentine stem weevil. Repell shows promise of excellent performance in both full sunlight and in light-to-moderate shade on lawns, parks, school grounds, and sports fields in areas where turf-type ryegrasses are well-adapted. Repell is also useful for the winter overseeding of dormant warm-season turfs.

Seed parent plants were selected from Central Park in New York City, N.Y., as the original maternal source of the performance-enhancing fungus within this variety. A pollen parent plant selected from U.S.D.A. PI No. 231,597 (Greece) was chosen for its resistance to crown rust disease, a desirable characteristic. Progeny from the cross which hosted the fungus were selected and then backcrossed with many desirable turf-type ryegrasses to incorporate as many useful characteristics as possible into the variety. Progeny from the backcross which hosted the fungus and which were resistant to crown rust were back-crossed again to many other desirable ryegrass plants. Progeny from this cross which hosted the fungus and which were crown-rust-resistant were selected for the third backcross.

The desirable ryegrass plants mentioned above included plants selected from the varieties "Manhattan," "Citation," and "Pennfine," in addition to other turf-type perennial ryegrasses selected from old turfs in Maryland, New Jersey, Pennsylvania, and New York. These plants had undergone two cycles of recurrent selection for crown rust resistance and improved turf performance before being used in the above crosses.

The third backcross involved large numbers of unrelated turf-type ryegrass parents. Progenies of the third backcross were subsequently subjected to two years of interplant competition in closely mowed turf plots. Tillers selected from the best plots were then established in an isolated spaced-plant nursery. The 27 parental clones of Repell were selected from this nursery based on attractive appearance, acceptable seed production, medium maturity, and freedom from disease.

Progenies of each clone were subsequently evaluated in turf trials subjected to frequent close mowing. Field evaluation for sod webworm resistance was also conducted at this stage. Tillers were then selected from 27 sod-webworm-resistant, endophyte-containing progenies showing the best turf performance and were transferred to an isolated spaced-plant nursery at Adelphia, N.J.

Seed from this nursery was used to establish an isolated spaced-plant nursery near Hubbard, Oregon, for production of breeder seed. This nursery was carefully rogued to improve uniformity of maturity, disease resistance, attractiveness of appearance, and seed yield. The first foundation seed of Repell was harvested in western Oregon in 1983. Seed production was limited to two generations of increase from breeder seed, one generation each of foundation and certified. Newly harvested seed or seed maintained in cold storage is used in the propagation of Repell to maintain the viability and effectiveness of the endophyte.

Deposit of Repell seed, under its experimental designation GT-II, was made on Nov. 14, 1983, prior to the filing of this application, at the U.S.D.A. National Seed Storage Laboratory, Colorado State University, Fort Collins, Colo. 80523, under Laboratory Accession No. LP-345, NSSL Serial No. 183,541.

What is claimed is:

1. A perennial ryegrass designated by the varietal name Repell, characterized by its persistent, dense, attractive, low-growing turf of a bright darkgreen color; its medium seed maturity; its medium-fine leaves; its excellent wear tolerance and very good heat, cold and drought hardiness; its resistance to large brown patch disease, winter leaf spot disease and crown rust disease; its resistance to sod webworms, billbugs, and Argentine stem weevils; and its hosting of a performance-enhancing endophytic fungus of the family Clavicipitaceae or Moniliaceae.

2. Seed of the perennial ryegrass of claim 1.

* * * * *